United States Patent [19]
Bombardelli et al.

[11] Patent Number: 5,973,163
[45] Date of Patent: Oct. 26, 1999

[54] OXAZOLIDINE CARBOXYLIC ACID INTERMEDIATES FOR ESTERIFICATION OF TAXANES

[75] Inventors: Ezio Bombardelli; Paolo De Bellis; Bruno Gabetta, all of Milan, Italy

[73] Assignee: INDENA S.p.A., Milan, Italy

[21] Appl. No.: 08/913,861

[22] PCT Filed: Mar. 4, 1996

[86] PCT No.: PCT/EP96/00904

§ 371 Date: Sep. 12, 1997

§ 102(e) Date: Sep. 12, 1997

[87] PCT Pub. No.: WO96/29321

PCT Pub. Date: Sep. 26, 1996

[30] Foreign Application Priority Data

Mar. 17, 1995 [IT] Italy .................................. MI95A0533

[51] Int. Cl.$^6$ ....................... C07D 263/06; C07D 305/14
[52] U.S. Cl. ........................... 548/215; 549/510; 549/511
[58] Field of Search ..................... 549/510, 511; 548/215

[56] References Cited

FOREIGN PATENT DOCUMENTS 0 577 083  1/1994  European Pat. Off. .
WO 95/01969  1/1995  WIPO .

OTHER PUBLICATIONS

Giovanni Appendino et al., Synthesis of Modified Baccatins via an Oxidation–Reduction Protocol, Tetrahedron Letters, vol. 36, No. 18 (May, 1995) pp. 3233–3236.

Giovanni Appendino et al., The Chemistry and Occurrence of Taxane Derivatives.XIII. The Oxidation of 10–Deacetyl-baccatin III, Gazzetta Chimica Italiana, vol. 124, No. 6 (Jun., 1994) pp. 253–257.

Zhang Hongjie et al., Taxol Related Diterpenes From the Roots of Taxus Yunnanensis, Heterocycles, vol. 38, No. 5 (1994) pp. 975–998.

*Primary Examiner*—Ba K. Trinh
*Attorney, Agent, or Firm*—Pennie & Edmonds LLP

[57] ABSTRACT

The present invention relates to novel oxazolidinecarboxylic acids. These oxazolidinecarboxylic acids are useful intermediates for the esterification of taxane synthons to provide taxanes esterified with an isoserine residue.

1 Claim, No Drawings

OXAZOLIDINE CARBOXYLIC ACID INTERMEDIATES FOR ESTERIFICATION OF TAXANES

This is a 371 application of PCT/EP96/00904 dated Mar. 4, 1996.

TECHNICAL FIELD

The invention relates to novel derivatives of 10-deacetylbaccatine III and of 10-deacetyl-14β-hydrobaccatine III having cytoxic and anti-tumoral activity as well as to methods for the preparation of these compounds.

BACKGROUND OF THE INVENTION

It is already well known that Paclitaxel (taxol), is a diterpenoid extracted from plants of the Taxus genus having anticancerogenic activity on different forms of human tumours. Its clinical use still involves some drawbacks due to the poor water solubility, which makes its administration complex, paclitaxel is also known to cause serious side effects. Moreover, paclitaxel induces resistance quickly. Due to these reasons, researches have been in progress for some years aiming at synthesizing novel paclitaxel analogues which cause less adverse effects compared with the parent molecule. WO-A-9501969 describes taxoids oxidized in position 10 and variously substituted in position 7 and 13. EP-A-577 083 describes cyclopropantaxanes variously substituted in positions 10 and 13.

"Gazzetta Chimica Italiana",124, 1994, describes methods for oxidizing the hydroxyl of 10-deacetylbaccatine III. "Heterocycles", Vol. 38 No. 5, 1994, describes new taxol related diterpenes isolated from the roots of *Taxus Yunnanensis* (Taxiyunnanine A).

SUMMARY OF THE INVENTION

The present invention relates to novel derivatives having a taxane skeleton endowed with a marked anti-tumoural activity. The novel derivatives have the general structure 1:

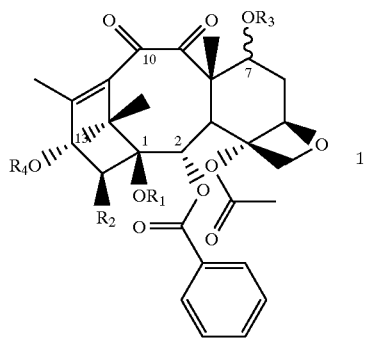

1 wherein $R_1$ and $R_2$ are hydrogen atoms, or $R_1$ is a hydrogen atom and $R_2$ is a hydroxyl or a acetyloxy group, or $OR_1$ and $R_2$ together form a cyclic carbonate group having the formula:

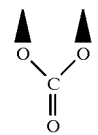

$R_3$, which can be α- or β-oriented, is a hydrogen atom or an alkylsilyl group, preferably triethylsilyl (TES); $R_4$ is hydrogen, or the residue

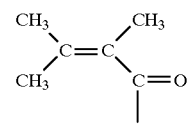

or an isoserine residue of formula A:

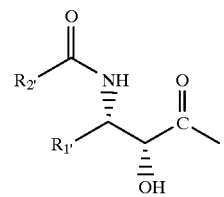

(A)

wherein $R_1'$ is a straight or branched alkyl or alkenyl group, containing one to five carbon atoms, or an aryl residue; $R_2'$ is a straight or branched alkyl or alkenyl group, containing one to five carbon atoms, or an aryl residue, or a tert-butoxy group.

The novel derivatives of general formula (1) are prepared by semisynthesis, starting from the natural syntons 10-deacetylbaccatine III (2) and 10-deacetyl-14β-hydroxybaccatine III (3). They are selectively oxidized in position 10 and then esterified in position 13 with a suitable acylating agent which allows the introduction of the group $R_4$.

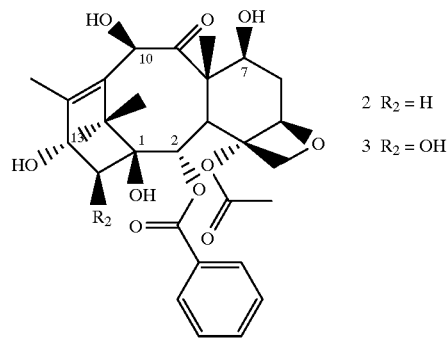

2 $R_2$ = H

3 $R_2$ = OH

When taxanes of natural or synthetic origin already contain the desired isoserine chain in position 13, the molecules of structure 1 can be obtained from these taxanes by selective oxidation in position 10. As described hereinafter, the selective oxidation in position 10 of 2, 3 and of the taxanes already containing the isoserine chain in position 13, can be obtained by treatment with copper (II) salts.

DETAILED DESCRIPTION OF THE INVENTION

As disclosed in U.S. Pat. No. 5,269,591, 10-Deacetylbaccatine III (2) and its 14β-hydroxy (3) analogs can be recovered from suitably selected vegetable material.

However, it is one of the objects of the present invention, to synthesize taxane syntons containing an oxygenated function in position 14, which are useful for the preparation of compounds of structure 1, containing an oxygenated function in position 14, starting from 10-deacetylbaccatine III (2). In fact, it has surprisingly been found that, after protecting the hydroxyl in position 7 of compound 2 as a silyl ether, the oxidation to ketone of the carbon in 13 and the introduction of a β-oriented alcohol function on the carbon in 14 take place by treatment with manganese dioxide. After protection of the hydroxyls in 10 and 14, for example as acetates, by treatment with hydrides, the 13-keto function is reduced to 13α-hydroxy.

The process, which is shown schematically below, leads to the formation of synton 4, which is used for the preparation of compounds with structure 1.

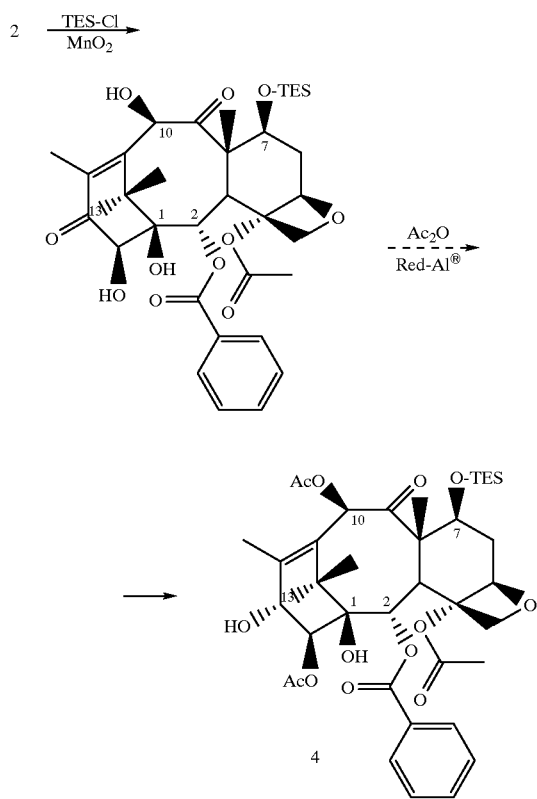

From synton 4, after removing the protective groups with known methods described in literature, for example using hydrochloric acid to remove the silyl group and a base to remove the acetate groups, 10-deacetyl-14β-hydroxybaccatine III (3) is obtained. Therefore, as mentioned, in order to prepare compounds of formula 1, 10-deacetylbaccatine III (2), 10-deacetyl-14β-hydroxybaccatine III (3), natural or semisynthetic, or other taxanes having an hydroxyl function at 10 and already containing in position 13 the isoserine chain represented by the group $R_4$, must be available.

It has surprisingly been found that all these syntons, by treatment with copper (II) salts, preferably copper acetate, undergo a selective oxidation in position 10, without need for the protection of the other hydroxyl functions. For example, 10-deacetylbaccatine III (2), 10-deacetyl-14β-hydroxybaccatine III (3) and the natural taxane 10-deacetylcephalomannine give the respective 10-keto derivatives 5–7 in yields from 75 to 85%. The oxidation generally requires protracted times (100–140 hours) and an oxidizer excess, and it is carried out at room temperature and in alcoholic solvent.

5  $R_1 = R_2 = R_3 = R_4 = H$

6  $R_1 = R_3 = R_4 = H; R_2 = OH$

8  $R_1, R_2 = \text{---CO---O}; R_3 = R_4 = H$

7  $R_1 = R_2 = R_3 = H; R_4 =$

When, preparing the compound of formula 1 according to the present invention, the presence of a cyclic carbonate group between positions 1 and 14 is required, synton 3 is previously treated with phosgene in pyridine and the resulting carbonate is then oxidized in position 10 with copper (II) acetate, to give carbonate synton 8.

When treated with bases, diketones 5–8 undergo an inversion in position 7, i.e. the hydroxyl in position 7 becomes α-oriented. Syntons 5, 6 and 8' or optionally their epimers in position 7, are therefore used for the preparation of taxanes of structure 1, after protection of the alcoholic functions present. The alcohol function in position 13, contrary to the other hydroxyalcohol functions, is poorly reactive to silylation and therefore does not undergo derivatization.

For the esterification in position 13, suitably activated isoserine chains are used, as reported in literature for the semisynthesis of paclitaxel and of its analogs (see. for example Eur. Pat. Appl. 400971, 1992; U.S. Pat. Nos. 5,175,315 and 5,336,785; Fr. Dem. 86, 10400; E. Didier et al., Tetrahedron letters 35, 2349, 1994; E. Didier et al.; ibid 35, 3063, 1994). Preferably, isoserin chains are used in the activated forms of oxazolidinecarboxylic acids 9a and 9b.

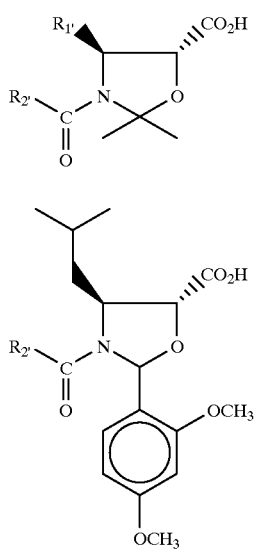

In formulae 9a and 9b, $R_1'$ and $R_2'$ have the meaning described above. The esterification of the oxazolidinecarboxylic acids with the taxane syntons and the subsequent elimination of the protective groups are carried out as described in literature for the synthesis of paclitaxel and the analogs thereof, as would be well known to those of ordinary skill in this field.

Among the compounds of formula 1, prepared according to the invention compounds 10, 11 and 12 were found to be particularly active. Compound 10 is 13-[(2R,3S)-3-ter-butoxycarbonylamino-2-hydroxy-3-isobutyl-propanoyl]-10-deacetyl-10-dehydro-baccatine III. Therefore, referring to general formula 1, compound 10 has: $R_1=R_2=H$, $OR_3=\beta$-OH, $R_1'$=iso-But, $R_2'$=t-BuO. Compound 11 is 13-[(2R,3S)-3-ter-butoxycarbonylamino-2-hydroxy-3-isobutyl-propanoyl]-10-dehydro-10-deacetyl-14β-hydroxy-baccatine III 1,14-carbonate. Therefore 11, referring to general formula 1, has $R_1$, $R_2$=—CO—O, $OR_3=\beta$-OH, $R_1'$=iso-But, $R_2'$=t-BuO.

Compound 12 is 13-[(2R,3S)-3-caproylamino-2-hydroxy-3-isobutyl-propanoyl]-10-dehydro-10-deacetyl-β-hydroxy-baccatine III 1,14-carbonate. Therefore 12, referring to general formula 1, has $R_1$, $R_2$=—CO—O, $OR_3$=B-OH, $R_1'$=iso-But, $R_2'=C_5H_{11}$.

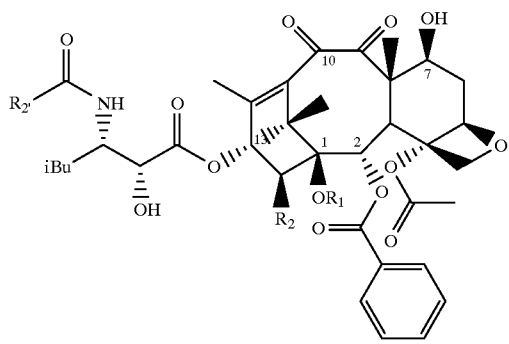

10 $R_1=R_2$ =H, $R_2'$=t-butoxy
11 $R_1$, $R_2$=CO—O, $R_2'$=t-butoxy
12 $R_1$, $R_2$=CO—O, $R_2'=C_5H_{11}$ The cytotoxicity data for compounds 10 and 11 compared with those for paclitaxel are reported in the following Table.

TABLE $IC_{50}$s of compounds 10, 11 and paclitaxel on 6 human tumour cell lines.

| Cell line | Exposition time (h) | Paclitaxel | $IC_{50}$ (nM) 10 | 11 |
|---|---|---|---|---|
| L1210 (murine leukemia) | 48 | 7.0 ± 3.0 | 0.6 ± 0.1 | 2.0 ± 0.1 |
| A121 (human ovarian) | 72 | 3.7 ± 0.3 | 0.8 ± 0.3 | 1.6 ± 0.2 |
| A549 (human NSCLC) | 72 | 5.4 ± 0.5 | 1.9 ± 0.3 | 2.1 ± 0.3 |
| HT-29 (human colon) | 72 | 6.0 ± 0.6 | 0.4 ± 0.1 | 0.6 ± 0.4 |
| MCF7 (human breast) | 72 | 4.3 ± 0.1 | 1.2 ± 0.2 | 0.8 ± 0.2 |
| MFC7-ADR (resistant) | 72 | 395 ± 8.7 | 13 ± 2.2 | 28 ± 6.2 |

Standard conditions: basal medium = RPMI 1640 ® + 20 mM HEPES + 2 mM L-Glutamine.

Compounds of formula 1 show surprising advantages compared with paclitaxel on cell lines resistant to other anti-tumoural substances, such as adriamycin or cis-platinum. The differences between paclitaxel and these products are even more evident in in vivo models, such as athymic nude mouse with human tumour implant. Moreover, it has been found that the compounds of the invention in which $R'_2$ is an alkyl or alkenyl group are surprisingly devoid of cardiotoxic activity, contrary to taxol and the known derivatives thereof, and therefore they can advantageously be used in the treatment of tumours in cardiopathic patients who cannot be treated with taxol and its previously known derivatives.

The products produced according to the invention can be incorporated in suitable pharmaceutical formulations for the administration of the products both parenterally and orally. For intravenous administration, mixtures of Chremoform L and ethanol, polysorbates or liposomial preparations prepared with natural or synthetic phosphatidylcholine or mixtures of natural phospholipids in the presence of cholesterol are mainly used.

The Examples following examples further illustrate the invention.

These examples are provided only for purposes of illustrating the invention and are not to be construed as limiting the invention in any manner.

EXAMPLE 1

Preparation of 10-deacetyl-10-dehydrobaccatine III (5).

10 g of 10-deacetylbaccatine III (2), (isolated as described by G. Chauviere et al., C.R. Acad. Sci,. Ser. II 293. 591. 1981) are suspended in 350 ml of methanol and combined with 65 g of $Cu(OAc)_2$. The suspension is stirred at room temperature for 120 h. The salts are filtered off and the solution is chromatographed on 100 g of silica gel eluting with a hexane/ethyl acetate 6:4 mixture. Upon crystallization from ligroin, 9.5 g of (5) are obtained, $M^+$a m/z 542.

EXAMPLE 2

Preparation of 10-deacetyl-10-dehydro-14β-hydroxybaccatine III 1,14-carbonate (8).

10 g of 10-deacetyl-14β-hydroxybaccatine III (3), isolated as described by G. Appendino et al., J. Chem. Soc. Perkin Trans I, 2925. 1992, are dissolved in 50 ml of anhydrous pyridine and treated for one hour with 1.5 eq. of 5% phosgene in toluene at −10° C. The reaction mixture is poured onto ice and the aqueous suspension is extracted with ethyl acetate, after which the organic phase is throughly washed with diluted HCl. After drying over $Na_2SO_4$ the organic phase is concentrated to dryness. 9 g of 1,14-carbonate are obtained, which are suspended in 350 ml of methanol and treated with 50 g of $Cu(OAc)_2$ with stirring at room temperature for 120 h. The suspension is filtered and the solution is evaporated to dryness. The residue is chromatographed on 100 g of silica gel eluting with a hexane/ethyl acetate 1:1 mixture. 8 g of compound (8) are obtained, $M^+a$ m/z 584.

EXAMPLE 3

Preparation of 13-[(2R,3S)-3-ter-butoxycarbonylamino-2-hydroxy-3-isobutyl-propanoyl]10-deacetyl-10-dehydrobaccatine III (10)

A solution of 300 mg (1.84 mmol) of 7-0-triethylsilyl-10-deacetyl-10-dehydrobaccatine III, obtained from compound (5) (Example 1) by silylation in position 7 with the method described by J. Denis et al., J. am. Chem. Soc. 100, 5917, (1988) in 60 ml of toluene is combined with 500 mg of (4S, 5R)-N-(ter-butoxy-carbonyl)-2.2-dimethyl-4-isobutyl-5-oxazolidineecarboxylic acid, 240 mg of dicyclohexylcarbodiimide (1.2 eq.) and 24 mg of N,N-dimethylaminopyridine (0.2 eq). The reaction mixture is kept at 80° C. for 2 hours, then is filtered and washed with water; the organic phase is concentrated to dryness. The residue is treated with methanol containing 0.1% of $H_2SO_4$ at 10° C. The methanol solution is diluted with water and the product is extracted with ethyl acetate; the organic phase is concentrated to dryness and the residue is chromatographed on silica gel eluting with acetone/hexane 4:6. 350 mg of compound (10) are obtained. $M^+a$ m/z 785.

EXAMPLE 4

Preparation of 13-[(2R,3S)-3-tert-butoxycarbonyl-amino-2-hydroxy-3-isobutyl-propanoyl]10-deacetyl-10-dehydro-14β-hydroxybaccatine III 1,14-carbonate (11).

0.5 g of 7-O-triethylsilyl-10-deacetyl-10-dehydro-14β-hydroxybaccatine III 1,14-carbonate, obtained from compound (8) (Example 2) by silylation in position 7 according to method reported by J. Denis et al., J. Am. Soc. 100, 5917 (1988) are dissolved in 60 ml of toluene. The solution is combined with 800 mg of (4S,5R)-N-(tert-butoxycarbonyl)-2.2-dimethyl-4-isobutyl-5-oxazolidinee-carboxylic acid, 400 mg of cyclohexylcarbodiimide and 40 mg of N,N-dimethylaminopyridine. The reaction mixture is kept at 80° C. for two hours, then is filtered and washed with water and the organic phase is concentrated to dryness. The residue is treated with methanol containing 0.1% of $H_2SO_4$ at 10° C. The methanol solution is diluted with water and the product is extracted with ethyl acetate; the organic phase is concentrated to dryness and the residue is chromatographed on silica gel, eluting with acetone/hexane 4:6. 580 mg of compound (11) are obtained, $M^+a$ m/z 827.

EXAMPLE 5

Preparation of 10-deacetyl-10-dehydro-14β-hydroxybaccatine III (6).

10 g of 10-deacetyl-14β-hydroxybaccatine III (3) are suspended in 350 ml of methanol and combined with 65 g of $Cu(OAc)_2$. The suspension is stirred at room temperature for 120 h. The salts are filtered off, the solution is evaporated to dryness and the residue is chromatographed on 100 g of silica gel eluting with a hexane/ethyl acetate 6:4 mixture. Upon crystallization from ligroin, 9.3 g of compound (6) are obtained, $M^+a$ m/z 558.

EXAMPLE 6

Preparation of 10-deacetyl-10-dehydro-cephalomannine (7).

0.4 g of 10-deacetylcephalomannine (J. L. Laughlin et al., J. Nat. Prod. 44. 312. 1981) are dissolved in 5 ml of MeOH and combined with 600 mg of $Cu(OAc)_2$. The reaction mixture is stirred for 54 hours at room temperature. The salts are filtered off, the solution is evaporated to dryness and chromatographed on silica gel (10 g) using a hexane-acetate diethyl 1:1 mixture as eluent 220 mg of compound (7) are obtained, $M^+a$ m/z 829.

EXAMPLE 7

Preparation of 7-triethylsilyl-14β-hydroxybaccatine III (4)

500 mg of 7-triethylsilyl-10-deacetylbaccatine III, prepared according to the method of J. Denis et al., J. Am. Chem. Soc. 100, 5917 (1988 ) are dissolved in 15 ml of a ethyl acetate-methylene chloride 9:1 mixture. The solution is combined with 10 g of $MnO_2$ leaving the suspension at room temperature under stirring for 24 hours. After filtration, the solution is evaporated to dryness and the residue is chromatographed on silica gel (20 g) eluting with a hexane-ethyl acetate 8:2 mixture. 310 mg of 7-triethylsilyl-10-deacetyl-13-dehydro-14β-hydroxybaccatine III are obtained ($M^+a$ m/z 672).

300 mg of this product are dissolved in 2 ml of pyridine. The solution is added with 910 mg of $Ac_2O$. After 16 hours the reaction mixture is poured onto ice and then extracted with ethyl acetate. The organic phase is washed with diluted HCl and then with water to neutrality. After evaporation of the solvent, the residue is crystallized from ether (220 mg, $M^+a$ m/z 756). The solid is dissolved in 10 ml of anhydrous THF; the solution is combined with 160 µl of sodium bis(2-methoxy-ethoxy)aluminium hydride (65% solution). After about 10 minutes, 10 ml of a $NH_4Cl$ saturated solution are added, extracting then with ethyl acetate. The organic phase is evaporated to dryness. The residue is purified on silica gel (15 g) eluting with a hexane-ethyl acetate 7:3 mixture. 80 mg of compound (4) are obtained, $M^+a$ 716.

EXAMPLE 8

Preparation of (4S,5R)-N-caproyl-2-(2.4-dimethoxyphenyl)-4-isobutyl-5-oxazolidinee carboxylic acid methyl ester.

5 g of N-caproyl-β-isobutyl-isoserine methyl ester are dissolved in 200 ml of a mixture of anhydrous THF and benzene and the solution is treated with 2 equivalents of 2.4-dimethoxy benzaldehyde dimethyl acetate in the presence of 120 mg of pyridinium p-toluenesulfonate. The solution is refluxed for 1 hour. The solvent is distilled and the residue is chromatographed on silica gel eluting the main compound with a ethyl acetate/hexane 8:2 mixture. After removing under vacuum the solvent from the fractions containing the desidered isomer, the residue is crystallized from hexane/isopropyl ether. 2.5 g of a compound having m.p. 98° C. are obtained.

Example 9

Preparation of (4S,5R)-N-caproyl-2-(2.4-dimethoxyphenyl)-4-isobutyl-5-oxazolidinee carboxylic acid 2 g of the compound of Example 8 are suspended in 50 ml of a mixture of methanol water (8:2) containing 5 g of K₂CO₃. The reaction mixture is stirred until complete dissolution of the isoserine derivative. The reaction mixture is carefully acidified to pH 5. with stirring, in the presence of ethyl acetate. The aqueous phase is discarded, whereas the organic phase is dried over sodium sulfate and concentrated to dryness at low temperature under vacuum. The residue is dissolved in a toluene/methylene chloride mixture and it is ready for the reaction with the selected taxanes.

EXAMPLE 10

Preparation of 13-[(2R,3S)-3-caproylamino-2-hydroxy-3-isobutyl-propanoyl]-10-dehydro-10-deacetyl-14β-hydroxy-baccatine III 1,14-carbonate (12)

5 g of 1,14-carbonate-7-TES-10-dehydro-baccatine III are dissolved in 100 ml of a mixture of toluene and methylene chloride in a 8:2 ratio, together with 6 g of (4S,5R)-N-caproyl-2-(2.4-dimethoxyphenyl)-4-isobutyl-5-oxazolidinee carboxylic acid. The reaction mixture is combined with 500 mg of 4-dimethylaminopyridine and 2.5 g of 1.3-dicyclohexylcarbodiimide, then heated for 2 hours under mild reflux until the reagents disappear. The compounds insoluble in the medium are filtered off and the solution is concentrated to dryness. The residue is taken up with 50 ml of methanol/HCl (0.01%) and the reaction mixture is left at room temperature for 1 hour. The solution is alkalinized to pH 5 and concentrated to dryness in a vacuum. The residue is chromatographed on a silica gel column eluting with a methylene chloride/methanol 98:2 mixture. Upon crystallization from ethyl acetate, 1.2 g of compound (12) are obtained.

| Example 11 - Solution of compound (10) for parenteral administration | |
|---|---|
| Compound 10 | 2 mg |
| Cremophor EL | 175 mg |
| Absolute alcohol q.s. to | 0.4 ml. |
| Example 12 - Solution of compound (11) for parenteral administration | |
| Compound 11 | 2 mg |
| Cremophor EL ® | 175 mg |
| Absolute alcohol q.s. to | 0.4 ml. |
| Example 13 - Tablets containing compound (10) | |
| Compound 10 | 10 mg |
| Cross-linked sodium carboxymethyl cellulose | 15 mg |
| Lactose (spray dried) | 41.5 mg |
| Microcrystalline cellulose | 40 mg |
| Colloidal silicon dioxide | 0.5 mg |
| Magnesium stearate | 1 mg. |
| Example 14 - Tablets containing compound (11) | |
| Compound 11 | 10 mg |
| Cross-linked sodium carboxymethyl cellulose | 15 mg |
| Lactose (spray dried) | 41.5 mg |
| Microcrystalline cellulose | 40 mg |
| Colloidal silicon dioxide | 0.5 mg |
| Magnesium stearate | 1 mg. |
| Example 15 - Capsules containing compound (10) | |
| Compound 10 | 10 mg |
| Lactose (spray dried) | 30 mg |
| Microcrystalline cellulose | 48.5 mg |
| Pre-gelatinized starch | 10 mg |
| Magnesium stearate | 1 mg |
| Colloidal silicon dioxide | 0.5 mg. |
| Example 16 - Capsules containing compound (11) | |
| Compound 11 | 10 mg |
| Lactose (spray dried) | 30 mg |
| Microcrystalline cellulose | 48.5 mg |
| Pre-gelatinized starch | 10 mg |
| Magnesium stearate | 1 mg |
| Colloidal silicon dioxide | 0.5 mg. |

We claim:
1. Intermediates of formula 9b

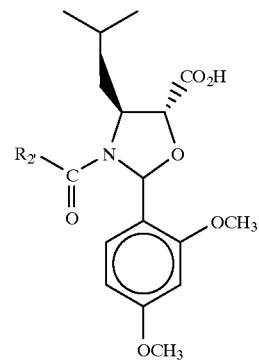

9b wherein $R_2'$ is a straight or branched alkyl or alkenyl group, containing one to five carbon atoms, or an aryl residue, or a tert-butoxy group.

* * * * *